United States Patent [19]

Henderson et al.

[11] Patent Number: 5,211,252

[45] Date of Patent: May 18, 1993

[54] AUTOMATIC BASIS SHEET WEIGHT AND MOISTURE CONTENT MEASURING APPARATUS

[75] Inventors: Richard M. Henderson, Winston-Salem; Tonya R. Young, Welcome; Tommy L. Hickman, Kernersville, all of N.C.; W. Richard Clendaniel, Andover, Mass.; Edward L. Dickinson, Acton, Mass.; Patsy A. Coppola, Bedford, Mass.

[73] Assignee: R. J. Reynolds Tobacco Company, Winston-Salem, N.C.

[21] Appl. No.: 837,848

[22] Filed: Feb. 18, 1992

[51] Int. Cl.[5] .................... G01G 19/40; G01G 19/52
[52] U.S. Cl. .................... 177/25.14; 177/50; 177/245; 364/568
[58] Field of Search ............ 177/25.14, 50, 245; 364/568

[56] References Cited

U.S. PATENT DOCUMENTS

| | | | |
|---|---|---|---|
| 3,536,258 | 10/1970 | Rocheleau | 364/568 |
| 3,564,224 | 2/1971 | Chope | 364/568 X |
| 3,590,826 | 7/1971 | Wochnowski et al. | 177/70 X |
| 3,909,598 | 9/1975 | Collins et al. | 177/25.14 X |
| 4,421,126 | 12/1983 | Gellatly | |
| 4,674,519 | 6/1987 | Keritsis et al. | |
| 4,771,631 | 9/1988 | Lehtikoski et al. | 177/50 X |
| 4,880,018 | 11/1989 | Graves, Jr. et al. | |
| 4,987,906 | 1/1991 | Young et al. | |
| 5,007,440 | 4/1991 | Robinson et al. | |

OTHER PUBLICATIONS

Tobacco Encyclopedia, compiled and edited by Ernst Voges, pp. 389-390, TJI (1984).

Primary Examiner—George H. Miller, Jr.
Attorney, Agent, or Firm—Grover M. Myers

[57] ABSTRACT

An apparatus for automatically measuring the basis weight and moisture content of a wet reconstituted tobacco web is disclosed. A specimen of the wet web is placed on a cutting surface of the apparatus and smoothed flat. A cutter is automatically positioned by a joy stick over the specimen and a test sequence is initiated. The cutter cuts out a sample of known area and transports the sample to a scale for weighing the sample in its wet and dry states. After the wet weight of the sample is entered into a computer, a heater dries out the sample while it remains on the scale. When the sample is dried, its dry weight is entered into the computer. Based on the wet and dry sample weights and the known sample area, the basis weight and moisture content of the reconstituted tobacco web is calculated by the computer. A disposal device removes the spent sample from the scale by suction and discards it into a waste receptacle.

17 Claims, 10 Drawing Sheets

AUTOMATIC BASIS SHEET WEIGHT AND MOISTURE CONTENT MEASURING APPARATUS

FIELD OF THE INVENTION

The present invention relates generally to the measurement of the basis weight and moisture content of a web of material, and more particularly to an apparatus for automatically measuring the basis weight and moisture content of a web of reconstituted tobacco.

DESCRIPTION OF THE PRIOR ART

In the manufacture of cigarettes and other smokable articles, reconstituted tobacco may be used as a tobacco component to be mixed with other shredded tobaccos to form a tobacco blend. Reconstituted tobacco is typically prepared in sheet form in a process akin to the manufacture of paper using modified paper making equipment. Such equipment processes tobacco stems, dust and other tobacco scrap materials and extracts water soluble components of the tobacco materials by a countercurrent extraction process. The water insoluble components, such as cellulosic fibers are refined in a pulp refining process. The refined pulp is directed to a wet forming machine which forms a paper-like sheet or web. The water soluble extract is concentrated according to a known process and applied to the wet web, for example, by spraying after which the web is dried to produce a finished sheet of reconstituted tobacco. The reconstituted tobacco is then formed into pieces which are blended with other tobacco pieces and cut into strands called cut filler.

One example of such a process for manufacturing reconstituted tobacco is described in U.S. Pat. No. 4,987,706 assigned to the assignee of this invention and the disclosure of which is incorporated herein by reference. In the manufacture of reconstituted tobacco, the amount of water soluble tobacco concentrate added to the base sheet per unit weight is an important parameter in forming an acceptable reconstituted tobacco product. Thus, the weight of the reconstituted tobacco sheet must be determined in order to control the amount of tobacco concentrate added to the sheet during the process. Typically, the weight parameter used to control the addition of concentrate to the sheet is the basis weight of the sheet, that is, the dry weight of the sheet per unit area which ranges from about 3.6 to about 4.2 grams/ft$^2$.

In the prior art, the basis weight was determined by manually extracting a specimen from the wet sheet or web prior to the addition of the tobacco concentrate. The specimen was then taken to a laboratory, where the specimen was manually cut into a sample having a predetermined area and then manually weighed, dried and reweighed. The basis weight and moisture content of the sheet were then calculated and, based on the calculated basis weight, the web manufacturing process was adjusted to apply the desired amount of concentrate to the web. One difficulty with this prior art procedure is that it results in a significant time lag from the time a sample is taken until a basis weight is determined and an adjustment can be made to the process. If an adjustment in the concentrate application rate is required, a considerable quantity of reconstituted tobacco sheet will have been made having a less than optimal content of tobacco concentrate.

The moisture content of the base sheet is also readily determined based on the difference between the wet and dry weights of the sample. The range of moisture content of the sheet prior to addition of the concentrate and drying of the base sheet is from about 40 to 80%. Based on the measured moisture content of the base sheet, the upstream dewatering process and the downstream drying process can be controlled so that the reconstituted tobacco sheet exits the dryer at or near the desired moisture content of about 10 to 15%.

SUMMARY OF THE INVENTION

The present invention is advantageously directed to an apparatus by which the wet machine operator can determine basis weight and moisture content with sufficient frequency and with a sufficiently short lag time to be of benefit in controlling machine operation without the need for a laboratory technician or a separate laboratory facility.

An automated, computer-controlled apparatus embodying the present invention includes a cutter for cutting out a sample of the base sheet having a known area, a pneumatic holder for picking up and releasing the sample, a transporter for moving the sample to a scale, a scale for weighing the sample during drying to obtain the wet and dry weights of the sample, an infrared lamp housed in a shroud or drying chamber for drying the sample, a pickup device for picking up and moving the dried and weighed sample from the scale to a disposal chute and a computer which receives inputs from the scale for calculating and displaying basis weight and moisture content of the base sheet.

One notable advantage of the apparatus of the present invention, apart from the speed and frequency with which the basis weight and moisture content can be determined, is the repeatability of results that is characteristic of an automatic measurement technique in which minimal human intervention is required.

With the foregoing and other advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
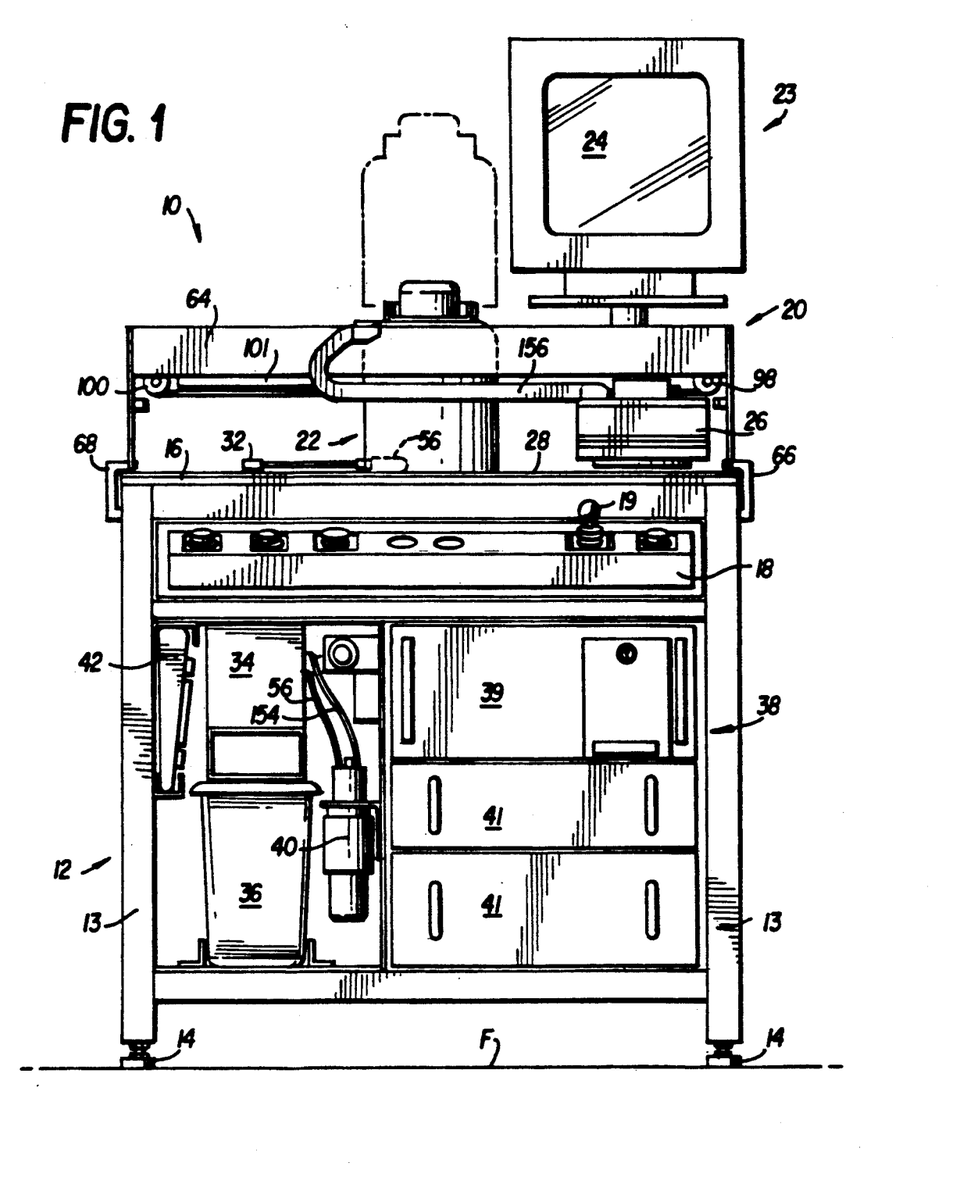
FIG. 1 is a front elevation view of a preferred embodiment of the apparatus of the invention with a front panel removed.
Figure 2:
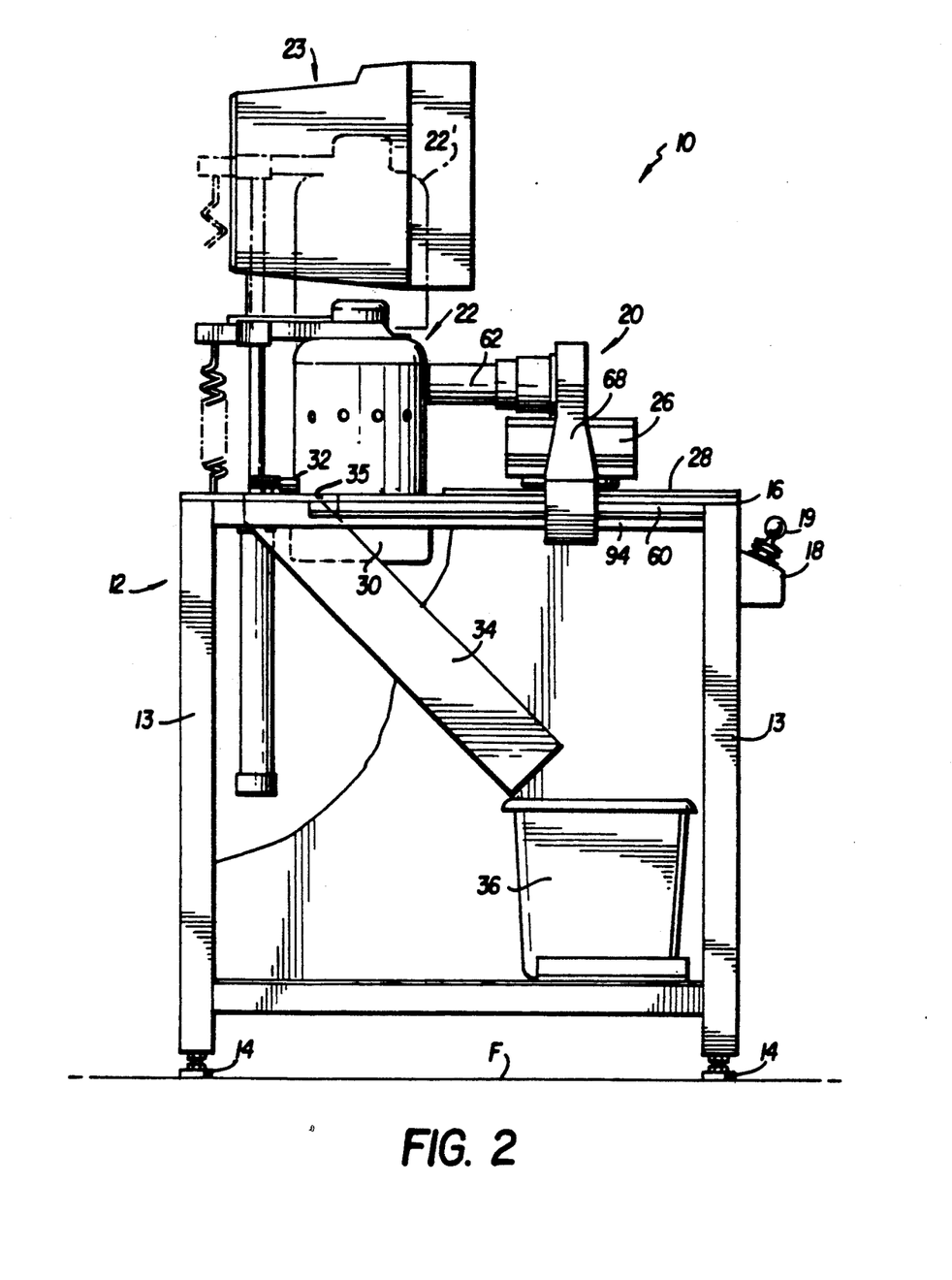
FIG. 2 is a side elevation view of the apparatus of the invention with a side panel removed.
Figure 3:
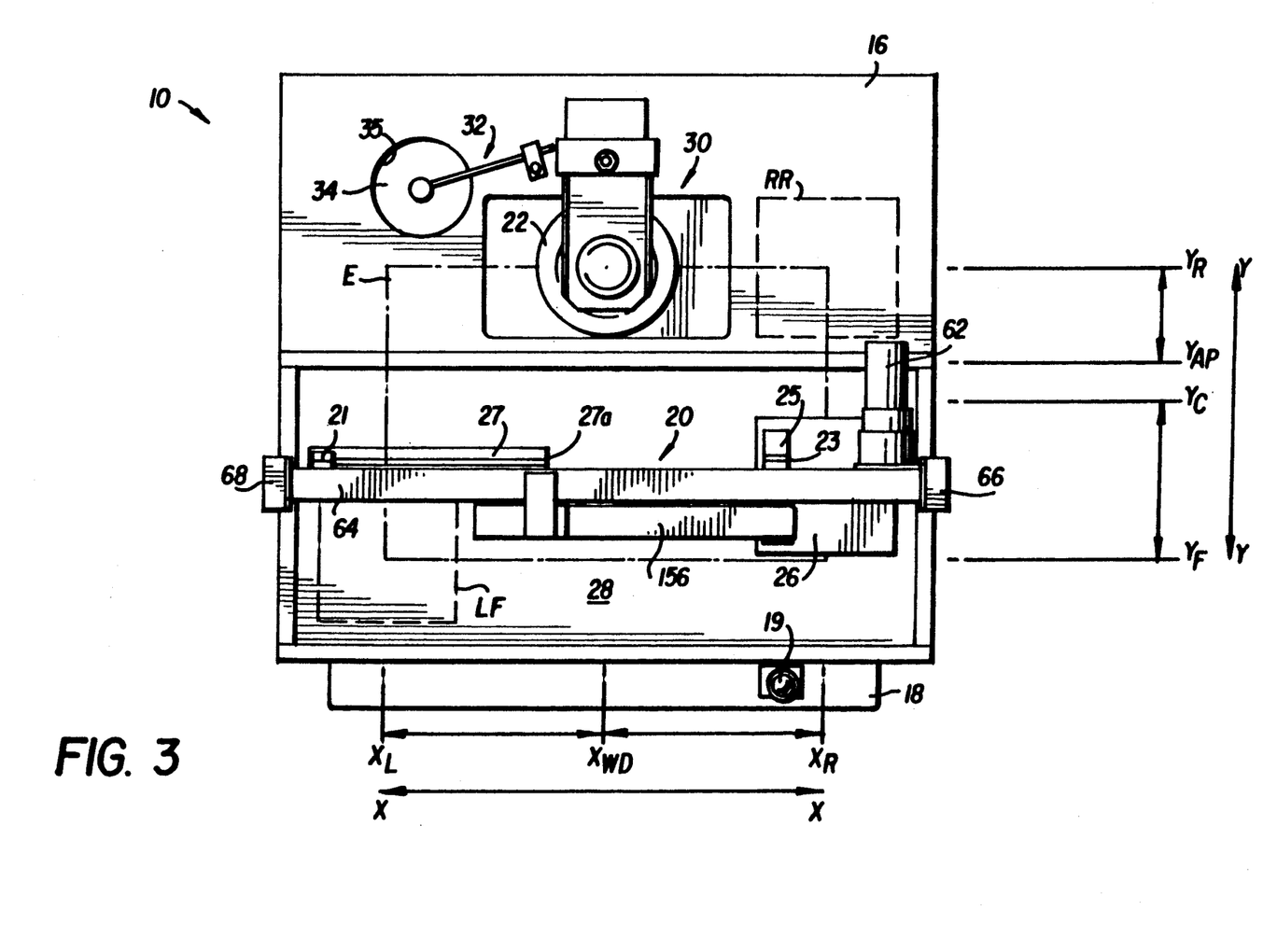
FIG. 3 is a top view of the apparatus of the invention.

Referring now in detail to the drawings wherein like parts are designated by like reference numerals throughout, there is illustrated in FIGS. 1-16 an apparatus embodying the present invention for automatically measuring sheet basis weight and moisture content of a wet sheet material, such as a reconstituted tobacco sheet. FIGS. 1-3 show the major components of the basis weight apparatus which is designated generally by reference numeral 10. A frame 12 having four legs 13 provides support for the components of the apparatus. Vibration isolators 14 mounted at the bottom of each leg 13 of the frame 12 serve to isolate the apparatus from external forces, such as vibrations from floor F, which might adversely affect the accuracy of the scale used to weigh samples.

Mounted to frame 12 are a table top 16, a control panel 18 which includes a joy stick 19, a gantry 20 which supports cutter assembly 26, a heater assembly 22, and a conventional video monitor 23 having a touch screen 24. Mounted to the table top 16 are cutting surface 28, scale 30, pickup device 32 and spent sample chute 34 which is accessible through an opening 35 in table top 16. A waste bin 36 receives spent samples from chute 34. An electronics cabinet 38 houses a computer 39 and control electronics 41. A vacuum pump 40 is mounted adjacent the electronics cabinet 38. A keyboard 42 is connected to the computer 39 and serves to perform testing and data entry functions for the system. The computer 39 is preferably an IBM AT computer or equivalent.

Generally, the apparatus 10 performs its automatic measurement function using a specimen of the wet reconstituted tobacco web which is manually taken in a conventional manner from an edge portion of the wet web as it moves through the transfer point between the press section of the wet machine and the spray section, upstream of the web dryer. This specimen has a surface area of about two to three square feet and is laid flat upon the cutting surface 28 of table top 16 and smoothed out by hand The apparatus 10 is then energized to automatically carry out a computer-controlled basis weight and moisture content measurement of the wet sheet using a sample of a predetermined area cut by the apparatus from the two to three square foot specimen of the wet sheet. The preferred sample according to the present invention is a circular sample having a six inch diameter and an area of about 0.196 ft$^2$. Although a larger or smaller area sample may be used, the six inch diameter sample provides better accuracy than a smaller area sample and is more easily transported, weighed and dried than a larger area sample, such as a square sample one foot on each side (1 ft$^2$) or a 1 foot diameter circular sample (0.785 ft$^2$).

Transport of the sample of the wet sheet in the direction of the X and Y axes is shown generally in FIG. 3, the X-axis direction being shown by the double-headed arrow X—X and the Y-axis direction being shown by the double-headed arrow Y—Y. FIG. 3 also shows cutter assembly 26 mounted on gantry 20, so as to be movable along gantry 20 in the X-axis direction. Gantry 20 is mounted on linear rails 58 and 60 (FIG. 4) which extend in the Y—Y direction. Mounted on gantry 20 is a drive motor 62 which actuates motion of cutter assembly 26 along gantry 20 in the X—X direction perpendicular to the Y—Y direction. The range or envelope of motion of the center of cutter assembly 26 is shown by the area encompassed by the dash-dotted line E in FIG. 3. Such envelope of motion E is required to position cutter assembly 26 over cutting surface 28 to obtain a cut sample of predetermined area, to permit the cut sample to be placed on scale 30, and then to permit the cutter assembly 26 to be moved out of the way so as not to interfere with the movement of heater assembly 22 or the pivotal motion of pickup device 32. Dashed line boxes RR and LF show, respectively, the rightmost-/rearmost and leftmost/forwardmost positions of the cutter assembly 26.

Figure 4:
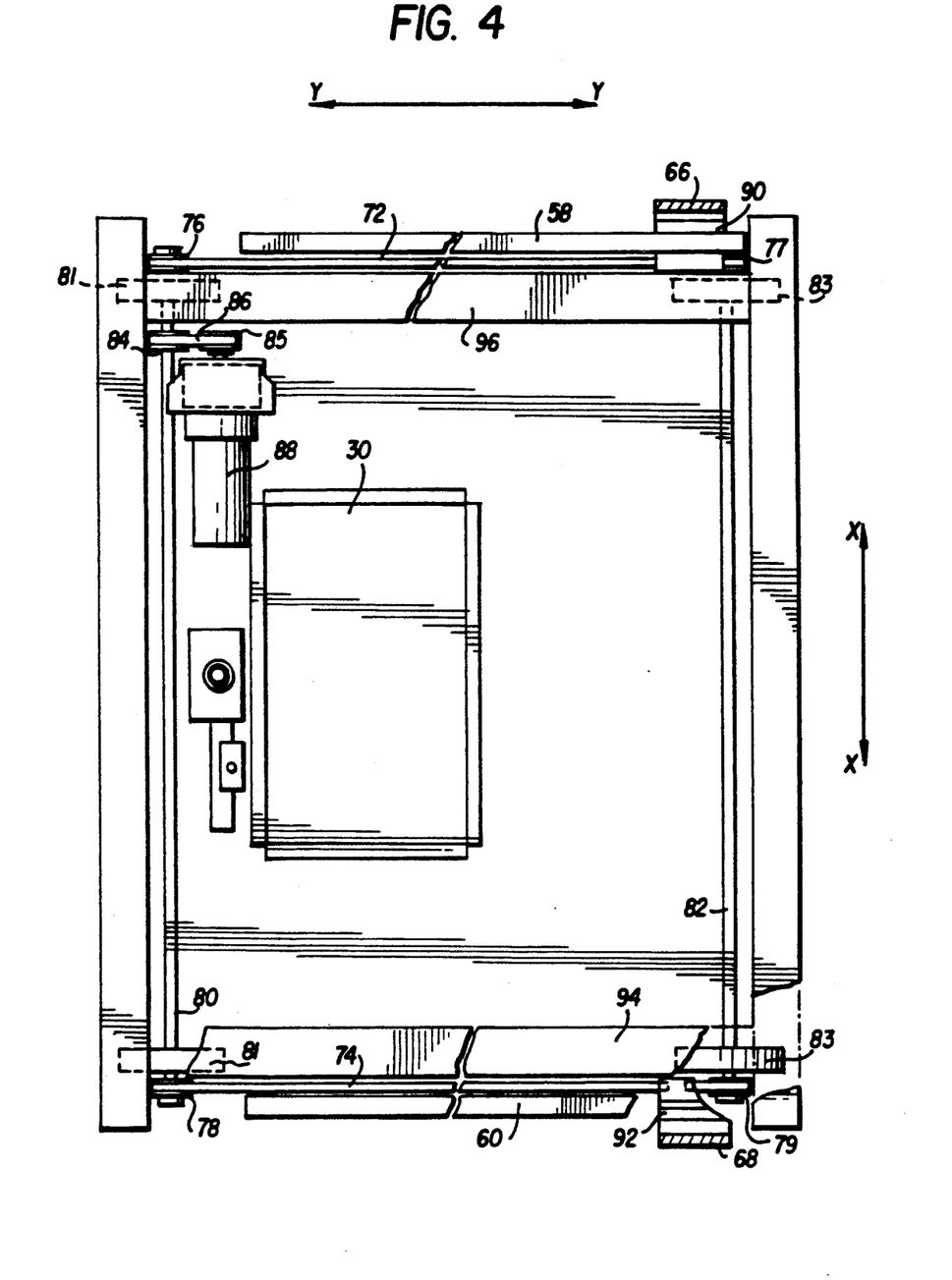
FIG. 4 is a top view, partly in cross-section, of a Y-axis drive for the cutter gantry support of the apparatus of the invention.
Figures 5, 6:
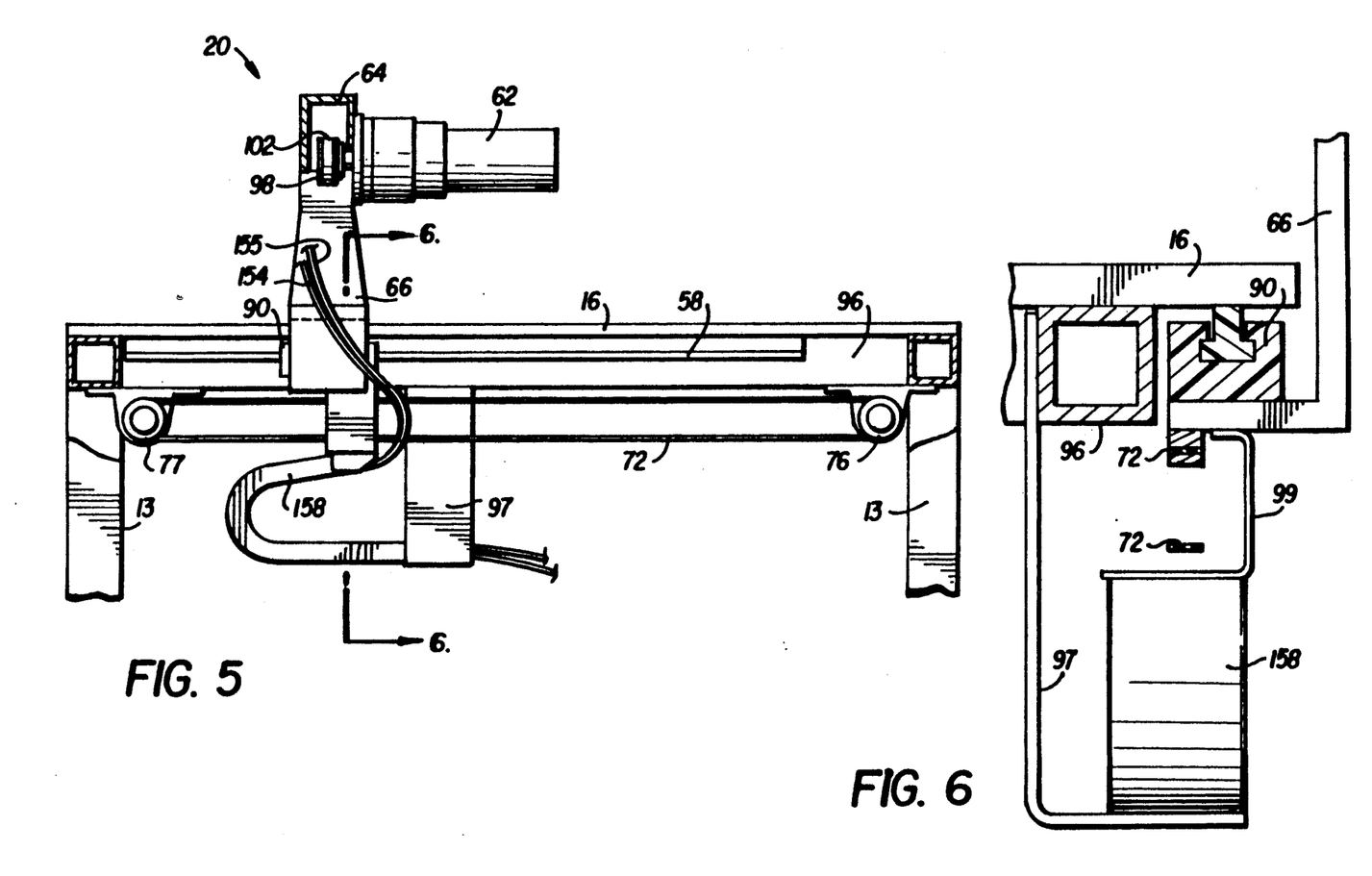
FIG. 5 is a side view, partly in cross-section, of the Y-axis drive of the invention.
FIG. 6 is a fragmentary detail of the Y-axis drive linear rail bearing.

As shown in FIGS. 4-6, the Y-drive subassembly is comprised of the gantry 20 having a gantry arm 64 supported by a pair of gantry side brackets 66, 68 mounted by means of guides 90, 92 on the parallel linear rails 58, 60, respectively. Each side bracket 66, 68 is attached to a respective toothed timing belt 72, 74 (FIGS. 4 and 6). Timing belts 72, 74 are 1/5 inch pitch ×⅜ inch wide belts and are trained about a respective pair of toothed pulleys 76, 77 and 78, 79 which are mounted at the opposite ends of parallel shafts 80, 82. Shafts 80, 82 are rotatably mounted in bearing blocks 81 and 83 A drive pulley 84 is fixedly mounted to shaft 80 and is driven by drive belt 86 trained about drive pulley 85 attached to the output shaft of a reversible motor 88 for moving the gantry 20 in the Y—Y direction. Reversible motor 88 is preferably a Model No. FH-PM motor manufactured by Robbins Myers of Minneapolis, Minnesota. Linear guide rails 58, 60 extend parallel to horizontal frame members 94, 96.

Figures 7, 10:
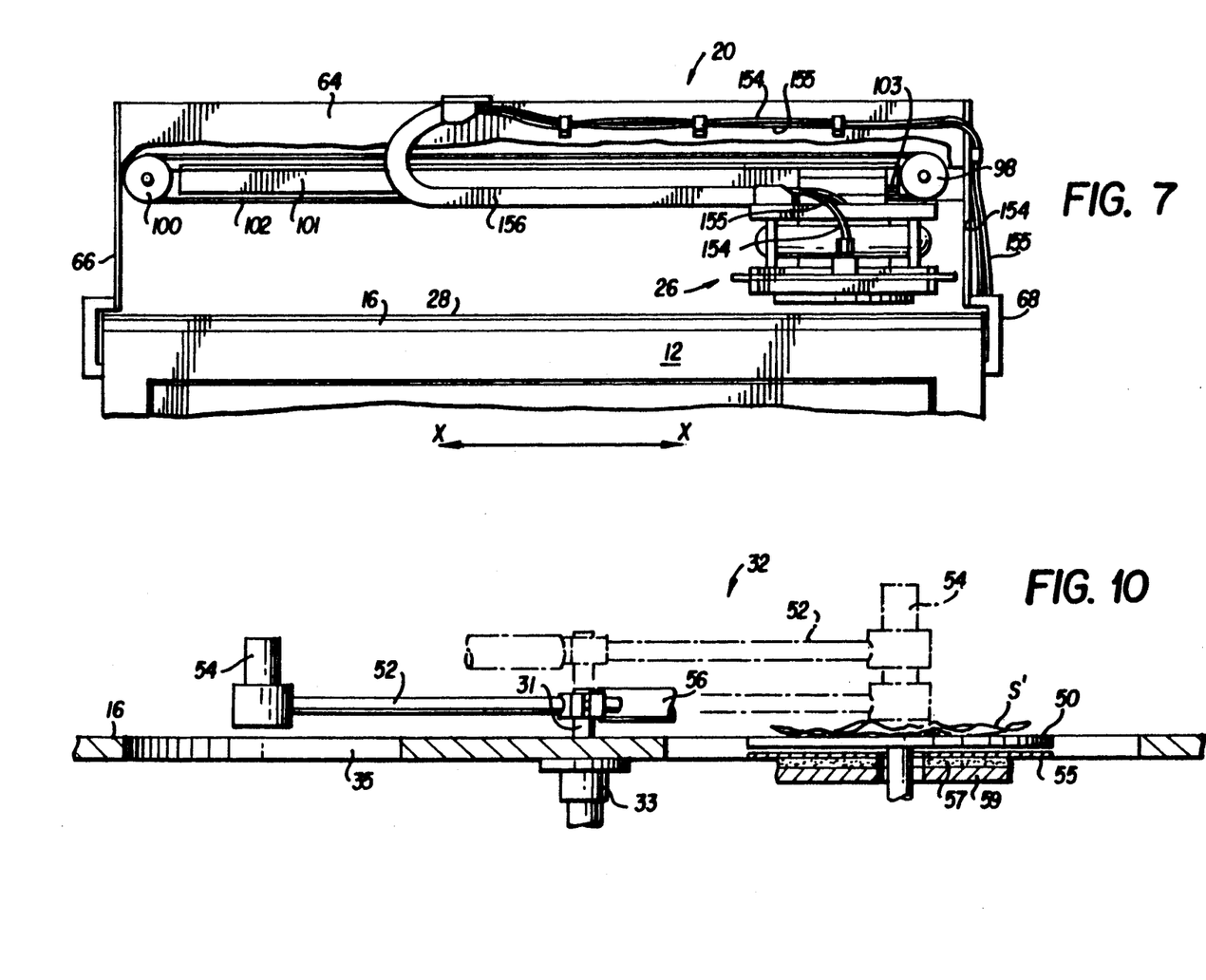
FIG. 7 is a fragmentary front view of the X-axis drive for the cutter assembly.
FIG. 10 is a fragmentary detail of the sample pickup device of the apparatus of the invention.

The X-drive mechanism for the cutter assembly 26 is shown in FIGS. 5 and 7. X-drive motor 62 is mounted to arm 64 of gantry 20 and is preferably the same type of reversible motor as motor 88. A toothed pulley 98 is mounted to the output shaft of motor 62 at one end of gantry arm 64 and another toothed pulley 100 is rotatably mounted at the other end of gantry arm 64. A 1/5 inch pitch ×⅜ inch wide toothed timing belt 102 is trained about the pulleys 98, 100. Cutter assembly 26 is suspended on a guide rail 101 mounted to the underside of gantry arm 64. Belt 102 is attached to cutter assembly 26 as at 103 (FIG. 7) so that as X-drive motor 62 is operated to rotate pulley 98, the belt 102 moves cutter assembly 26 back and forth along guide rail 101 in the X—X direction.

Figures 8, 9:
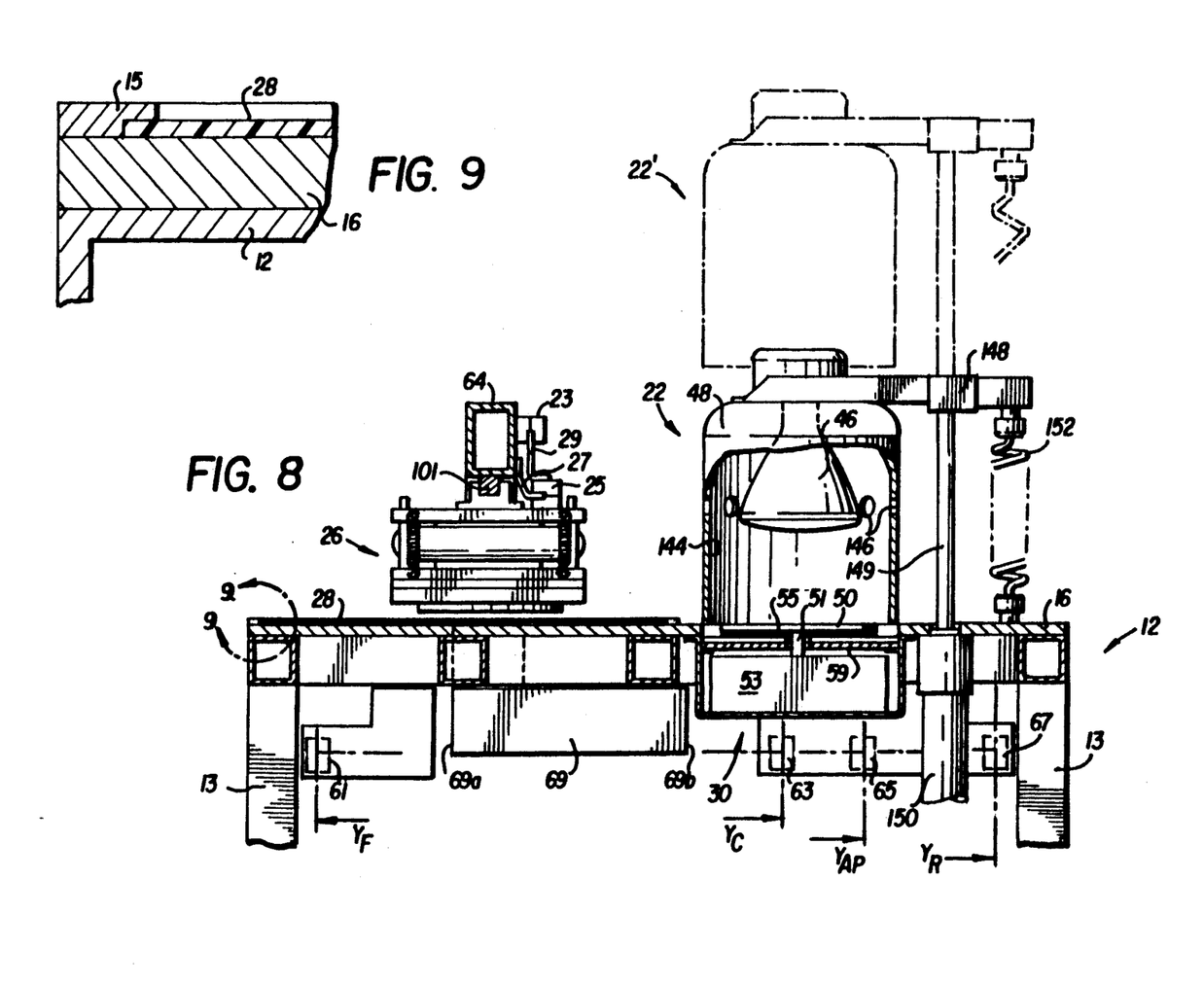
FIG. 8 is a side view, partly in cross-section, of the heater and cutter assemblies.
FIG. 9 is a fragmentary detail of the cutting table identified as detail 9—9 in FIG. 8.

The envelope of motion E is determined by the limits of movement of gantry 20 in the Y—Y direction and the movement of cutter assembly 26 along gantry 20 in the X—X direction. Movement of cutter assembly 26 in the X—X direction along gantry 20 is limited by two limit switches 21, 23 attached to gantry 20 and a flag 29 mounted on cutter assembly 26 (FIGS. 3 and 8). An elongated flag 27 attached to the rear side of gantry arm 64 and a position switch 25 mounted on cutter assembly 26 locates the sample weighing and drying position $X_{WD}$ (FIG. 3) of the cutter assembly 26. Detection of the flag 29 by the left limit switch 21 determines the left travel limit of the center of cutter assembly 26 shown as $X_L$ in FIG. 3. Similarly, detection of the flag 29 by the right limit switch 23 determines the right travel limit $X_R$ also shown in FIG. 3. The sample weighing and drying position $X_{WD}$ is determined by detection of the rightmost edge 27a of flag 27 by position switch 25. To avoid ambiguity as to the $X_{WD}$ position of the cutter assembly 26, the flag 27 must be elongated so that only the single edge 27a can be sensed by switch 25 between the limits of travel of the cutter assembly 26.

As shown in FIGS. 3 and 8, travel of gantry 20 in the Y—Y direction along linear rails 58, 60 is determined by limit switches 61, 63, 65 and 67 mounted on frame 12 beneath table top 16. Elongated flag 69 attached to and movable with gantry 20 is detected by the respective limit switches and determines the limits of motion of the gantry 20 and cutter assembly 26 in the Y—Y direction. Front travel limit $Y_F$ of the center of cutter assembly 26 shown in FIGS. 3 and 8 is determined by the detection of the front edge 69a of flag 69 by limit switch 61. Cutting area limit $Y_C$ is determined by limit switch 63 detecting the rear edge 69b of 69. Auto park or home position $Y_{AP}$ is determined by limit switch 65 detecting the rear edge 69b of flag 69. Finally, rear travel limit $Y_R$ is determined by limit switch 67 detecting the rear edge 69b of flag 69.

FIG. 9 shows a detail of the construction of cutting surface 28 mounted to table top 16. Table top 16 is preferably an aluminum jig plate mounted on frame 12. A cutting surface clamp 15 holds cutting surface 28 in place. Cutting surface 28 is preferably a hard, scratch resistant plastic material, such as a ⅛ inch sheet of white Delrin ® manufactured by Dupont of Wilmington, Delaware.

Figure 11:
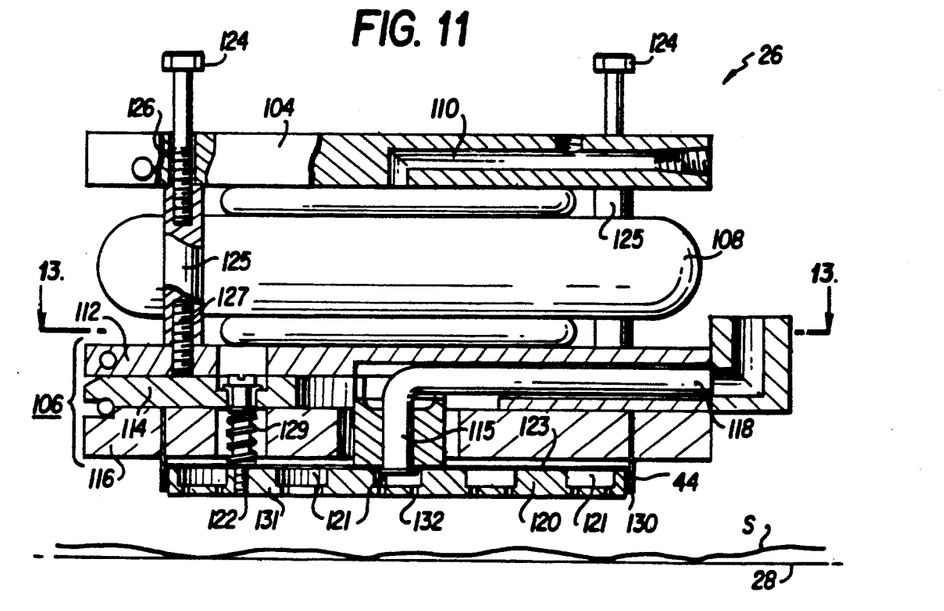
FIG. 11 is a cross-sectional view of the cutter assembly of the invention with the cutter blade in its retracted position.
Figure 12:
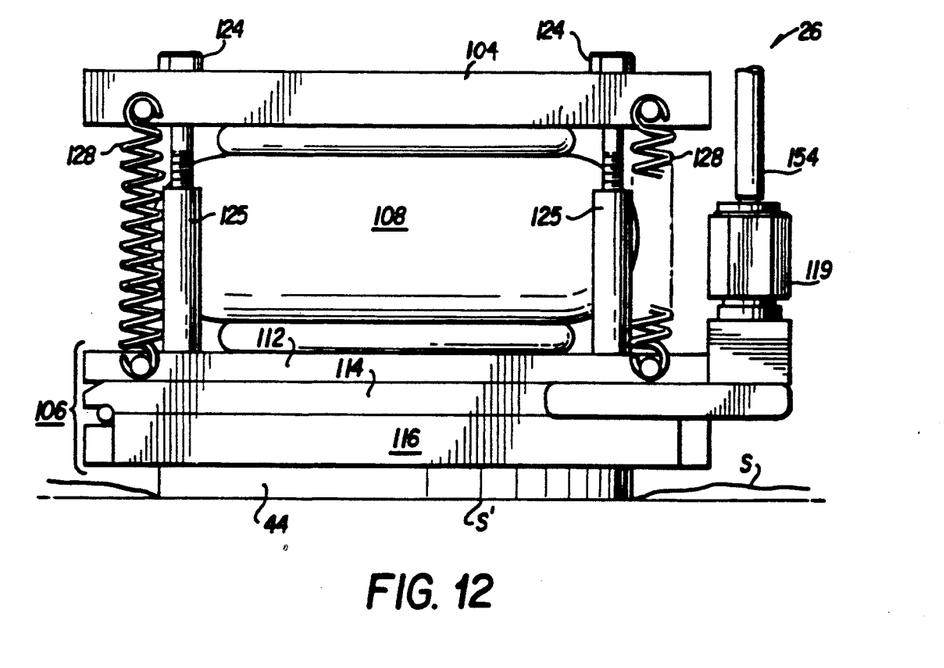
FIG. 12 is a cross-sectional view of the cutter assembly of the invention with the cutter blade in its extended position.
Figure 13:
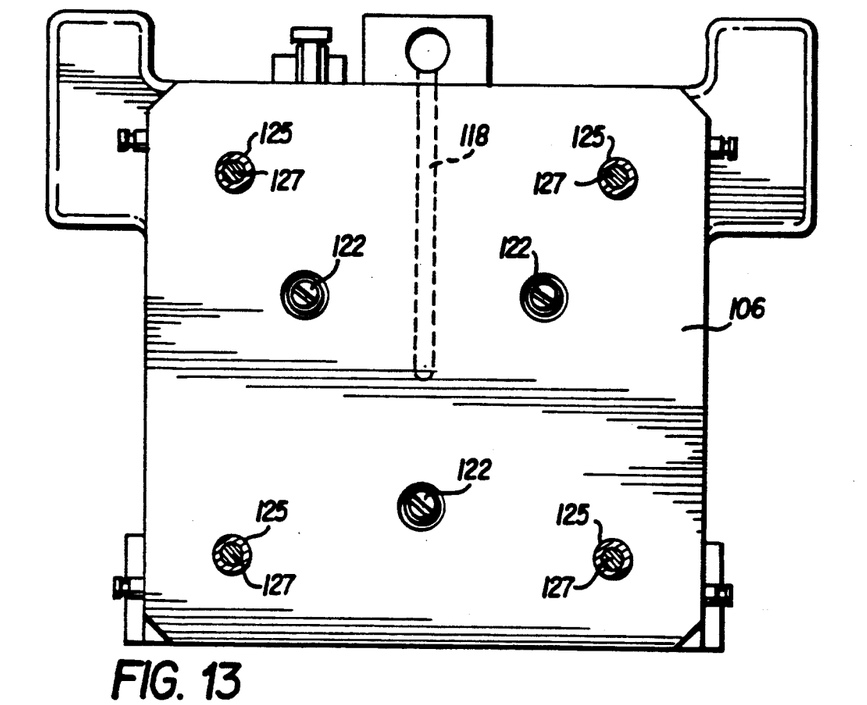
FIG. 13 is a cross-sectional view of the cutter assembly taken along line 13—13 of FIG. 11.

FIGS. 11-14 illustrate the components of the cutter assembly 26 which perform the cutting and lifting functions with FIGS. 11 and 12 showing the cutter assembly 26 in a disengaged and an engaged state, respectively. An upper plate 104 and lower plate assembly 106 have an inflatable bladder 108 disposed therebetween. Air supply conduit 110 is formed in upper plate 104 and communicates with an air inlet/outlet (not shown) of bladder 108. Bladder 108 is preferably an actuator Model No. 110-7451 manufactured by The Firestone Company of Akron, Ohio. Air pressure to bladder 108 via air supply conduit 110 is provided by any suitable source, (not shown), such as shop air. Typical pressures to inflate bladder 108 are in the range of 73-77 psi. Lower plate assembly 106 is comprised of three separate plates 112, 114 and 116 sandwiched together. Vacuum conduit 118 is formed within lower plate assembly 106. Fitting 119 mounted on lower plate assembly 106 and communicating with vacuum conduit 118 provides the attachment for a flexible vacuum line 154. Upper plate 104 and lower plates 112 and 114 are preferably made of aluminum or another metal. Lower plate 116 is preferably in the form of a steel rule die wherein the plate 116 is made of plywood and has disposed therein a steel rule cutter 44 in a circular shape having a six inch diameter.

Figure 14:
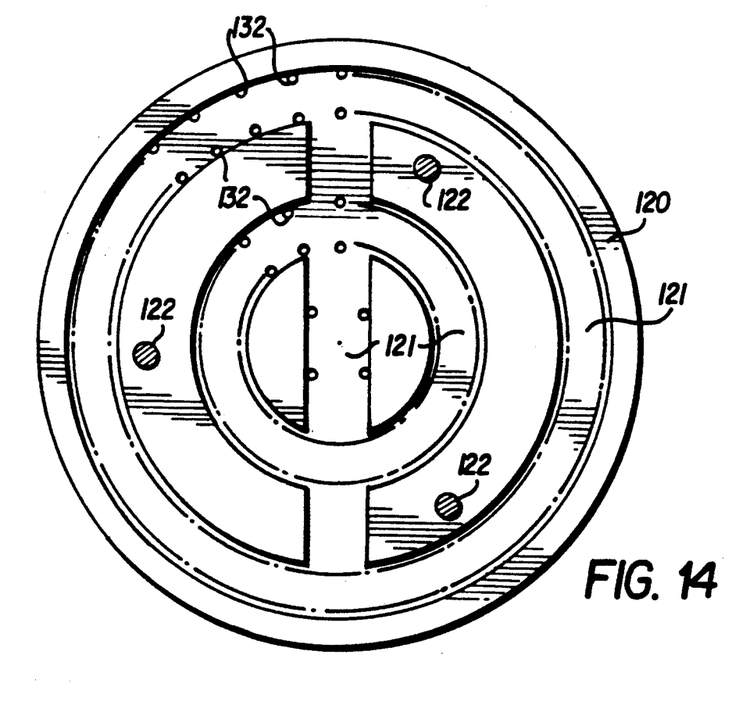
FIG. 14 is a cross-sectional view of the die platen taken along line 14—14 of FIG. 11.

A die platen 120 is suspended beneath lower plate assembly 106 by bolts 122 and is resiliently biased toward the cutting surface 28 by springs 129. Die platen 120 is preferably made of steel and as best seen in FIGS. 11 and 14 is provided with arcuate and diametric channels 121 which communicate with vacuum conduit 118 via a nipple 115. A cover plate 123 sealingly closes the upper sides of the channels 121 and forms a vacuum chamber on the upper side of die platen 120.

Upper plate 104 and lower plate assembly 106 are held in the spaced relationship of FIG. 11 by four posts 125 which are secured to plate 112 by threaded studs 127 and by springs 128 (FIG. 12) which urge plates 104 and 112 together. Four bolts 124 threaded into the upper ends of posts 125 are slidably disposed through holes 126 in upper plate 104 and adjustably limit the downward stroke of the lower plate assembly 106 and thus cutter 44 when the bladder 108 is inflated. See FIG. 12.

In operation, an air supply through conduit 110 to bladder 108 expands the bladder 108, thereby forcing lower plate assembly 106 downwardly until the downward motion is stopped by the heads of bolts 124 engaging the top surface of upper plate 104. Because cutter assembly 26 is mounted to the guide rail 101 fixed beneath gantry arm 64, the upper plate 104 remains fixed and does not move upwardly. As lower plate assembly 106 is forced downwardly, the lowermost face 131 of platen 120 contacts specimen S and forces it to lie flat against cutting surface 28. Because platen 120 is spring-biased relative to lower plate assembly 106, the springs 129 are compressed and the cutting edge 130 of cutter 44 is forced against the specimen S so as to cut out a six inch diameter sample in the manner of a steel rule die cutter. Vacuum drawn via vacuum conduit 118 creates a vacuum in the chamber formed by channels 121 and cover plate 123. This vacuum communicates with the six inch diameter sample S' (FIG. 12) through holes 132 in the bottom of the channels 121 of platen 120. After the sample S' is cut from the larger specimen S, the cutter assembly 26 is retracted by venting the air pressure in bladder 108 which permits biasing springs 128 to raise lower plate assembly 106 until the tops of posts 125 again engage upper plate 104 as shown in FIG. 11. The platen 120 is also extended by springs 129 downwardly beyond the cutting edge 130. Maintenance of vacuum in the chamber of platen 120 results in the sample S' being held in place on the bottom face 131 of platen 120 for transport to the weighing and drying station as described hereinafter.

The weighing function is accomplished by scale 30, which is preferably a Model No. PM 400 balance manufactured by Mettler Instrument Corporation of Highstown, New Jersey. FIG. 8 shows details of the arrangement of the scale 30. Scale platen 50 is mounted on a balance pin or shaft 51 which is attached to balance mechanism 53 of scale 30. Disposed beneath platen 50 and coaxially mounted around shaft 51 is a reflective plate 55, preferably made of polished aluminum. Disposed beneath reflective plate 55 are an insulative pad 57, preferably made of silicone sponge, and a support plate 59, preferably made of aluminum. Reflective plate 55 serves to reflect heat away from the balance mechanism 53 and into the drying chamber formed by shroud 48.

Figure 15:
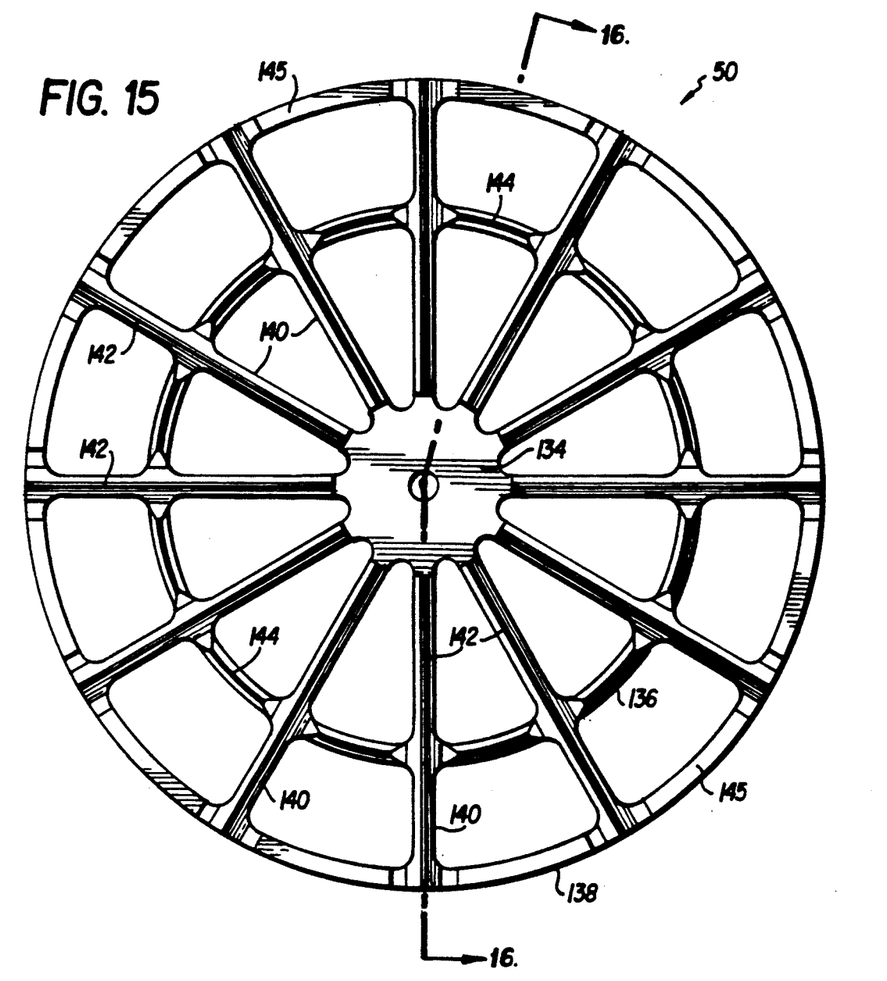
FIG. 15 is a top plan view of the scale platen.
Figure 16:
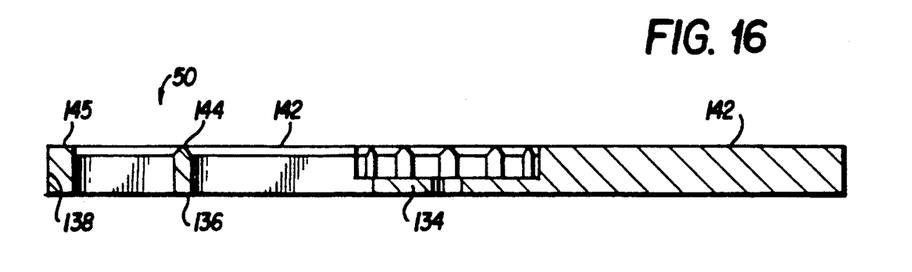
FIG. 16 is a cross-sectional view of the scale platen taken along line 16—16 of FIG. 15.

FIGS. 15 and 16 show a top and sectional view, taken along section A—A, respectively, of scale platen 50. Scale platen 50 is a circular arrangement comprising a hub 134, inner ring 136 and outer ring 138 with a plurality of radial spoke members 140 symmetrically arranged between hub 134 and outer ring 138. Each spoke 140 has a narrow central ridge 142, inner ring 136 has a similar narrow arcuate ridge 144 disposed between the spokes 140, and outer ring 138 has portions 145 coplanar with the upper surfaces of ridges 142 and 144. The purpose of this arrangement is to provide a relatively small surface area support for the sample S' and to permit even drying of the sample S' after heater assembly 22 is lowered over the sample S' as it rests on the platen 50 of scale 30.

The components of the apparatus 10 which perform the drying function are shown in detail in FIGS. 2, 3 and 8. FIG. 3 shows heater assembly 22 centered over scale 30. A partial cross-sectional view of heater assembly 22 is shown in FIG. 8. A heat lamp 46 is mounted within the shroud 48 of the heater assembly 22. Lamp 46 is preferably a 250 watt infrared lamp manufactured by Phillips Corp. of Somerset, New Jersey. Shroud 48 serves as a drying chamber and is a dome-shaped structure having a reflective inner coating 144 and a plurality of holes 146 for releasing water vapor which results from drying a wet sample with the infrared lamp 46. Heater assembly 22 is vertically movable between the solid line position and the dash-dot line position 22' shown in FIGS. 2 and 8. This vertical movement is accomplished by the raising and lowering of cantilever support arm 148 by means of the piston rod 149 of pneumatically actuated piston and cylinder assembly 150. Electrical power to lamp 46 is provided by flexible coiled power cord 152 attached to and carried by support 148.

The sample pickup and release function is performed by pneumatic components and is comprised of the vacuum pump 40 which is connected by a hose 154 to cutter assembly 26. A pressure hose 155 is also connected to cutter assembly 26 from shop air for example. Hoses 154, 155 are flexible and are carried in the X—X and Y—Y directions, respectively, by an articulatable cable guide 156 attached between cutter assembly 26 and gantry arm 64 (FIG. 7) and an articulatable cable guide 158 suspended at one end from frame member 96 by a bracket 97 and carried at its other end by a bracket 99 suspended from gantry side bracket 66 (FIGS. 5 and 6). Cable guide 156 is preferably a Model No. IGUS #10-3-038 manufactured by IGUS Bearing, Inc. of East Providence, Rhode Island and has 17 segments. Cable guide 158 is preferably an IGUS #10-4-038 also manufactured by IGUS and has 13 segments. The vacuum pump 40 acting via hose 154, vacuum conduit 118, channels 121 and the holes 132 in platen 120, provides a suction force to retain the wet circular sample S, on the lower face 131 of platen 120 for transport by the cutter assembly 26 to the platen 50 of the scale for weighing of the sample S'.

After the wet and dry weights of the sample S' have been read and entered into the computer 39, o disposal of the dried sample S, is accomplished by a pickup device 32 (FIG. 10) having a pivotal pickup arm 52 attached to a vacuum pickup head 54. Pickup head 54 is a venturi-type vacuum generator powered by air pressure from line 56. Pickup device 32 is mounted on the output shaft 31 of a partially shown pick-and-place actuator 33 Model No. PA 01-120-1.5-ZAR 4R-WA4-Style 8.75 in. manufactured by Rotomation of Daytona, Florida. The home position of pickup arm 52 is shown in solid lines in FIG. 10 and the pickup positions of the arm 52 are shown in dash-dot lines.

Operation of the apparatus of the present invention is as follows: In an initial standby condition of the apparatus 10, the cutter assembly 26 is located in its auto park or home position at $Y_{AP}$ (FIG. 3) and the heater assembly 22 is positioned over the scale 30 as shown in FIG. 8 for an initial heat up cycle. During the heat up cycle, an operator manually retrieves a specimen of the reconstituted tobacco sheet, preferably at a location between the wet machine and the dryer stage of the sheet making machinery. This manually retrieved specimen is preferably on the order of two to three square feet in area. The operator deposits the specimen onto the cutting surface 28 and manually smooths it to an essentially flat condition.

Using joy stick 19, the operator then moves gantry 20 and cutter assembly 26 in the X—X and Y—Y directions from the auto park position to a position where cutter assembly 26 is disposed over cutting surface 28 and confronting an acceptable region of the smoothed out specimen S. Once the cutter assembly 26 is properly positioned by the operator with joy stick 19, the remaining operations may be automatically controlled by computer 42 in a conventional manner upon initiation of a test cycle, e.g., by touching an appropriate touch pad on touch screen 24. When the test cycle is initiated, the bladder 108 of cutter assembly 26 is supplied with air pressure via hose 155 and conduit 110 to pneumatically inflate the same so that cutting edge 130 cuts a six inch diameter circular sample S' from the specimen S. During the cutting of the sample S', suction from vacuum pump 40 is applied to the vacuum chamber in platen 120 via hose 154 and vacuum conduit 118. When the air pressure in bladder 108 is vented at the end of the sample cutting step and the lower plate assembly 106 returns to its raised position above cutting surface 28 (FIG. 11), the sample S' will be held in place on the platen 120 by suction for transport by the cutter assembly to the weighing and drying station.

After the shroud 48 of heater assembly 22 is raised to position 22, (FIG. 8), gantry 20 is automatically moved in the Y—Y direction and cutter assembly 26 is moved in the X—X direction along gantry 20 so as to position the cut sample S' directly over the platen 50 of scale 30. The vacuum to platen 120 is then released thereby dropping the cut sample S' onto the scale platen 50. If necessary, a slight air pressure may be applied to the vacuum chamber in platen 120 to assist in dislodging the cut sample S' from the face 131 of the platen 120. Cutter assembly 26 is then automatically moved to its auto park or home position at $Y_{AP}$ so as to clear the space above the scale 30. Heater assembly 22 is then lowered over the cut sample S' such that shroud 48 completely encloses the sample, thereby forming a drying chamber.

A weighing and drying procedure is then initiated to determine the wet and dry weights of the cut sample S'. At the commencement of the weighing and drying cycle, electrical power is applied to infrared lamp 46 and the output of scale 30, which represents the wet weight of sample S', is read and entered into the computer 39. During the drying cycle, the output of scale 30 is periodically sampled by the computer 39, and when the rate of change of the sample weight decreases to a predetermined level indicating the sample S' has been dried to a substantially zero moisture content, the sample weight is again entered into the computer 39 and represents the dry weight of sample S'. Based on the measured wet and dry weights of the sample S' and the known area of sample S' which is also an input to the computer 39, the percent moisture of the reconstituted tobacco web and its basis weight in grams per square foot are calculated by the computer 39.

After the moisture content and basis weight have been calculated, displayed and stored, the drying cycle is terminated and sample discard sequence is initiated. Shroud 48 is raised by actuation of piston and cylinder assembly 150 to raised position 22, (FIG. 8) above the scale platen 50. Pickup device 32 is then raised from its storage or rest position over opening 35 (FIG. 10), and the pivotal pickup arm 52 is then rotated and lowered by pick-and-place device 33 to position the pickup head 54 over the dried cut sample S'. Suction from vacuum pump 40 is applied via hose 56 through the pickup device head 54 to pick up the dried cut sample S'. The arm 52 is then raised and rotated so that head 54 is positioned over opening 35 in table top 16. The dried spent sample is then released and dropped through opening 35, down spent sample chute 34 and into waste bin 36. The apparatus 10 is now ready to perform an analysis of another specimen. The calculations of basis weight and moisture content by the computer 39 may be displayed on screen 24 of monitor 23 and/or printed out on any suitable printer means (not shown).

Although a presently preferred embodiment of the invention has been described herein, it will be apparent to those skilled in the art to which the invention pertains that variations and modifications of the described embodiment may be made without departing from the spirit and scope of the invention. Accordingly, it is intended that this invention be limited only to the extent required by the appended claims and the applicable rules of law.

What is claimed is:

1. Apparatus for determining the basis weight and moisture content of a base sheet of reconstituted tobacco comprising:
   means for automatically cutting a sample of predetermined area from a wet specimen of the base sheet;
   means for automatically weighing the sample;
   means for automatically transporting the sample of predetermined area in a wet state to the weighing means and for depositing the sample on the weighing means;
   means for automatically drying the sample to a substantially dry state, said automatic weighing means being operative to automatically weigh the sample in its wet state and in its substantially dry state; and
   means for computing the moisture content and basis weight of the reconstituted tobacco sheet based on the wet and dry weights of the sample and the predetermined area thereof.

2. The apparatus of claim 1, wherein said automatic cutting means comprises a cutting surface for supporting the wet specimen of the base sheet, a cutter mounted above said cutting surface for vertically reciprocable movement with respect to said cutting surface, and means for urging said cutter against a wet specimen supported on said cutting surface to cut said sample of predetermined area from said specimen.

3. The apparatus of claim 2, wherein said urging means comprises an inflatable bladder and a pressure source for inflating said bladder.

4. The apparatus of claim 2, wherein said cutter comprises a steel rule die having a circular cutting blade for cutting a circular sample from the wet specimen of the base sheet.

5. The apparatus of claim wherein said automatic transporting and depositing means comprises means for pneumatically holding the cut sample on the cutting means and for releasing the cut sample from the cutting means and means for moving said cutting means in first and second directions at right angles.

6. The apparatus of claim 5, wherein said pneumatic holding and releasing means comprises a platen mounted to said cutting means, said platen having a substantially planar face for contacting the sample, vacuum means connected to said platen for holding the sample against the face of said platen by suction, and means for interrupting the vacuum to said platen to release the sample from the platen.

7. The apparatus of claim 1, wherein said weighing means includes a support for the sample, said automatic drying means comprises a shroud, a source of infrared energy mounted in said shroud and means for moving said shroud between a first position spaced above said weighing means and a second position covering at least said support for the sample.

8. The apparatus of claim 7, wherein said infrared source is an infrared lamp mounted in said shroud, said shroud moving means comprising a piston and cylinder assembly connected to said shroud for raising and lowering said shroud between said first and second positions.

9. The apparatus of claim 1, including means for automatically discarding the sample after the sample has been weighed in both its wet and dry states.

10. The apparatus of claim 9, wherein said automatic discarding means comprises a vacuum head pivotable between a sample pickup position and a sample discard position and a vacuum means connected to said vacuum head for picking up the sample by suction when the vacuum head is in the pickup position and for interrupting the vacuum to the vacuum head when the vacuum head is in the discard position.

11. An apparatus for determining the basis weight and moisture content of a base sheet in the manufacture of reconstituted tobacco sheet, comprising:
   a cutter assembly for cutting and holding a sample of reconstituted tobacco sheet having a known area;
   a gantry to which said cutter assembly is mounted for transporting said cutter assembly from a first location where the sample is cut to a second location where the sample is weighed;
   a scale for weighing the sample in both a wet state and in a dried state;
   a heater assembly including an infrared lamp and a shroud, said heater assembly being positionable over said scale so as to be adapted to dry a sample on said scale;
   a disposal device adapted to pick up a dried sample from said scale and discard the dried sample; and
   a computer for calculating the moisture content and basis weight of the sample based on the wet and dry weights of the sample and the known sample area.

12. The apparatus of claim 11, including a cutting surface, said cutter assembly further comprising a first plate, a second plate assembly, a bladder adapted to be inflated and deflated and disposed between said first plate and said second plate assembly, a steel rule die mounted on the underside of said second plate assembly and having a cutting edge forming a cutting perimeter for cutting the sample from a specimen of reconstituted tobacco sheet, a die platen disposed within said cutting perimeter and being resiliently mounted on the underside of said second plate assembly so as to be extendable from said second plate assembly to a point beyond said die cutting edge, whereby when said bladder is inflated, said second plate assembly is urged away from said first plate so that said die platen contacts the specimen on said cutting surface, said die platen is urged toward said second plate assembly and said die cutting edge cuts a sample from said specimen.

13. The apparatus of claim 12, including a vacuum chamber in said die platen, a vacuum source connected to said vacuum chamber, said die platen having holes therein communicating with said vacuum chamber to apply suction to the sample whereby when said bladder is deflated, said die platen moves away from the cutting surface and carries with it by suction the sample cut from the specimen.

14. The apparatus of claim 11, further comprising a first drive mechanism for moving said gantry in a first direction, and a second drive mechanism for moving said cutter assembly in a second direction along said gantry, said first and second directions being perpendicular to each other.

15. The apparatus of claim 11, wherein said scale comprises a platen having a hub, an inner ring, an outer ring and symmetrically arranged spokes emanating from said hub and connecting said inner ring and said outer ring, said inner ring, said outer ring and said spokes having ridge portions for supporting a sample placed thereon to be weighed.

16. The apparatus of claim 11, wherein said shroud is dome-shaped and has a plurality of holes for venting water vapor released from the sample as it is dried, and pneumatic means for raising and lowering the shroud over the scale.

17. The apparatus of claim 11, wherein said disposal device comprises a vacuum head and a pivot arm, a conduit formed through said head and arm, a vacuum source communicating with said conduit, and a pneumatically actuated shaft connected to said pivot arm for raising, lowering and pivoting said pivot arm and vacuum head.

* * * * *